(12) United States Patent
Batzer

(10) Patent No.: US 11,346,892 B2
(45) Date of Patent: May 31, 2022

(54) DETECTION OF SIGNAL PATH DEFECTS WHEN MEASURING BIOELECTRIC SIGNALS

(71) Applicant: Siemens Healthcare GmbH, Erlangen (DE)

(72) Inventor: Ulrich Batzer, Buckenhof (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 227 days.

(21) Appl. No.: 16/406,171

(22) Filed: May 8, 2019

(65) Prior Publication Data

US 2019/0353692 A1 Nov. 21, 2019

(30) Foreign Application Priority Data

May 15, 2018 (EP) .................................. 18172315

(51) Int. Cl.
*G01R 31/58* (2020.01)
*A61B 5/318* (2021.01)
(Continued)

(52) U.S. Cl.
CPC .............. *G01R 31/58* (2020.01); *A61B 5/318* (2021.01); *A61B 5/369* (2021.01); *A61B 5/389* (2021.01);
(Continued)

(58) Field of Classification Search
CPC .. G01R 19/00; G01R 19/16566; G01R 17/00; G01R 17/02; G01R 31/00; G01R 31/08;
(Continued)

(56) References Cited

U.S. PATENT DOCUMENTS 5,755,742 A 5/1998 Schuelke et al.
5,766,133 A 6/1998 Faisandier
(Continued)

FOREIGN PATENT DOCUMENTS

CN 101408581 A 4/2009
CN 102640374 A 8/2012
(Continued)

OTHER PUBLICATIONS

Anthony Calabria: "Understanding Lead-Off Detection in ECG". Texas Instruments, Application Report. SBAA196A, May 2012, Revised Jan. 2015. http://www.ti.com/lit/an/sbaa196a/sbaa196a.pdf.
(Continued)

*Primary Examiner* — Son T Le
(74) *Attorney, Agent, or Firm* — Harness, Dickey & Pierce, P.L.C.

(57) ABSTRACT

A fault detection device includes at least one electricity generating unit, to impress a signal on a first useful signal path; at least one first comparison unit, to determine if the signal of the first useful signal path lies within a measuring range; and at least one first interference signal path, designed as a current measurement path, for current-detecting measurement of a first interference signal. A signal path defect analysis unit, is included to detect a signal path defect, upon the impressed signal not being measured on the at least one first interference signal path and upon the checked signal of the comparison unit being determined to lie within the measuring range. Furthermore, corresponding methods are for the detection of signal path defects in a voltage measuring system for measuring bioelectric signals are defined.

24 Claims, 6 Drawing Sheets

(51) Int. Cl.
*A61B 5/369* (2021.01)
*A61B 5/389* (2021.01)

(52) U.S. Cl.
CPC . *A61B 2560/0276* (2013.01); *A61B 2562/222* (2013.01)

(58) Field of Classification Search
CPC ............... G01R 31/58; G01R 31/2836; G01R 31/3193; G01R 31/3275; G01R 23/005; A61B 5/0402; A61B 5/0476; A61B 5/0488; A61B 2560/0276; A61B 2562/222; A61B 5/7225; A61B 5/0428; A61B 5/04004; A61B 5/0424; A61B 5/7221
See application file for complete search history.

(56) References Cited

U.S. PATENT DOCUMENTS

| | | | |
|---|---|---|---|
| 9,316,678 | B2 | 4/2016 | Schaefer |
| 2003/0163170 | A1 | 8/2003 | Faisandier |
| 2012/0256637 | A1 | 10/2012 | Juhlin |
| 2016/0095528 | A1 | 4/2016 | Batzer et al. |
| 2016/0228024 | A1 | 8/2016 | Batzer et al. |
| 2017/0071548 | A1 | 3/2017 | Wiebe et al. |

FOREIGN PATENT DOCUMENTS

| | | |
|---|---|---|
| CN | 105339853 A | 2/2016 |
| DE | 19728902 A1 | 2/1999 |
| DE | 102014219943 A1 | 4/2016 |
| DE | 102015202447 A1 | 8/2016 |
| DE | 102017214862 A1 | 2/2019 |
| EP | 0944413 B1 | 2/2001 |

OTHER PUBLICATIONS

European Search Report (EPA Form 1507N 06.12) for European Application No. EP18172315 dated Nov. 11, 2018.
Office Action for Chinese Patent Application No. 201910405748.2 dated Mar. 1, 2021.
Office Action for Chinese Patent Application No. 201910405748.2 dated Sep. 3, 2021.
Office Action for European Patent Application No. 18172315.6 dated Nov. 4, 2021.

DETECTION OF SIGNAL PATH DEFECTS WHEN MEASURING BIOELECTRIC SIGNALS

PRIORITY STATEMENT

The present application hereby claims priority under 35 U.S.C. § 119 to European patent application number EP18172315.6 filed May 15, 2018, the entire contents of which are hereby incorporated herein by reference.

FIELD

Embodiments of the invention generally relate to a fault detection device; and/or to a method for the detection of signal path defects in a voltage measuring system, preferably a differential voltage measuring system, having a signal measuring circuit for measuring bioelectric signals with a number of useful signal paths. Embodiments of the invention also generally relate, moreover, to a voltage measuring system having a fault detection device of this kind.

BACKGROUND

Voltage measuring systems, in particular differential voltage measuring systems, for measuring bioelectric signals are used for example in medicine for measuring electrocardiograms (ECG), electroencephalograms (EEG) or electromyograms (EMG). With such applications, preferably a high input impedance of at least several MOhm should be observed on any measuring channel in order to reduce, or at least not to amplify, the effect of interference. The high, sought input impedance should also be maintained in the cables of the above-mentioned devices for measuring bioelectric signals. Conventionally, the measuring leads of cables are surrounded by a shield. To obtain better handleability the cables are also flexible, narrow and light. These features lead, however, to a conflict between the life and the handleability of the cables and increase the risk of a cable defect.

The causes of defective cables are for example broken leads or often kinks. Kinks can occur after a torsion or bending of the long cables if the measuring leads bulge and do not return to their original form. The bulging measuring leads can then break through the lead insulation and contact the shield, and this can lead to a reduced input impedance in the cables and therewith to an intensification of interference. The problem here is that, without a special test environment such interference may not always be clearly attributed to a reduced input impedance in the cables. In addition kinks and other input impedance-reducing cable defects often occur as loose connections, and this similarly makes fault detection difficult. There is therefore the risk that a defective cable will unintentionally be worked with until the signal quality is no longer sufficient to be able to carry out bioelectric measurements and examinations.

A common solution for avoiding or detecting interference by way of a reduced input impedance in the cables is to replace the cables at regular intervals or at least have them examined by service personnel. On checking of the cables by service personnel, a reference signal generated by a simulator is emitted to the cable to be examined. The cable is then moved and an output signal is measured. This output signal is compared with the reference signal and checked as to whether there are differences between the two signals and therefore interference. The interference with which a cable break is assumed is based on expert opinion, however. This checking is relatively laborious, moreover.

In U.S. Pat. No. 5,766,133 voltage measurements are made on cables of an ECG measuring system in order to detect a cable break.

SUMMARY

Embodiments of the present invention provide a device and/or a method to detect signal path defects, in particular cable defects, in a voltage measuring system.

Embodiments of the present invention are directed to a fault detection device, a voltage measuring system and by a method.

An embodiment of the present invention is directed to a fault detection device for the detection of signal path defects in a voltage measuring system including a signal measuring circuit for measuring bioelectric signals with a number of useful signal paths, the fault detection device comprising:
  at least one electricity generating unit, to impress a signal on a first useful signal path;
  at least one first comparison unit, to determine if the signal of the first useful signal path lies within a measuring range;
  at least one first interference signal path, designed as a current measurement path, for current-detecting measurement of a first interference signal; and
  a signal path defect analysis unit, to detect a signal path defect in a useful signal path of the voltage measuring system upon the impressed signal not being measured on the at least one first interference signal path and upon the checked signal of the comparison unit being determined to lie within the measuring range.

An embodiment of the present invention is directed to a voltage measuring system, comprising:
  at least one signal measuring circuit, including a number of useful signal paths for measuring bioelectric signals; and
  the fault detection device of an embodiment.

An embodiment of the present invention is directed to a method for the detection of signal path defects in a voltage measuring system for measuring bioelectric signals, the bioelectric signals being measured via a signal measuring circuit including a number of useful signal paths, the method comprising:
  impressing at least one first signal on at least one first useful signal path, of the number of useful signal paths, via at least one first electricity generating unit;
  determining, via at least one first comparison unit, whether the signal of the at least one first useful signal path lies within a measuring range;
  current-detecting measurement of at least one first interference signal on at least one first interference signal path designed as a current measuring path; and
  performing an analysis, via a signal path defect analysis unit, to detect a signal path defect in a useful signal path of the number of useful signal paths of the voltage measuring system, upon the impressed signal not being measured on the at least one first interference signal path and upon the signal being determined, via the comparison unit, to lie within the measuring range.

A large proportion of the above-mentioned components of the voltage measuring device, in particular the signal path defect analysis unit, can be wholly or partially implemented in the form of software modules in a processor of a corresponding voltage measuring system. An implementation largely in terms of software has the advantage that even previously used voltage measuring systems can be easily retrofitted by way of a software update in order to operate inventively. In this regard the object is also achieved by a corresponding computer program product having a computer program, which can be loaded directly into a storage device of a voltage measuring system, having program segments in order to carry out all steps of at least one embodiment of the inventive method when the program is run in the voltage measuring system.

In addition to the computer program, at least one embodiment is directed to a computer program product of this kind can optionally comprise additional components, such as, for example documentation and/or additional components also hardware components, such as, for example hardware keys (dongles, etc.) in order to utilize the software.

A computer-readable medium, for example a memory stick, a hard disk or another portable or permanently fitted data carrier, on which the program segments of the computer program, which can be read-in and executed by an arithmetic unit of the voltage measuring system are stored, can be used in at least one embodiment for transportation to the voltage measuring system and/or for storage on or in the voltage measuring system. The arithmetic unit can have one or more cooperating microprocessor(s) or the like for this purpose.

BRIEF DESCRIPTION OF THE DRAWINGS

The invention will be explained in more detail again below with reference to the accompanying figures using example embodiments. Identical components are provided with identical reference numerals in the various figures.

As a rule, the Figures are not to scale. In the drawings.

DETAILED DESCRIPTION OF THE EXAMPLE EMBODIMENTS

Figure 1:
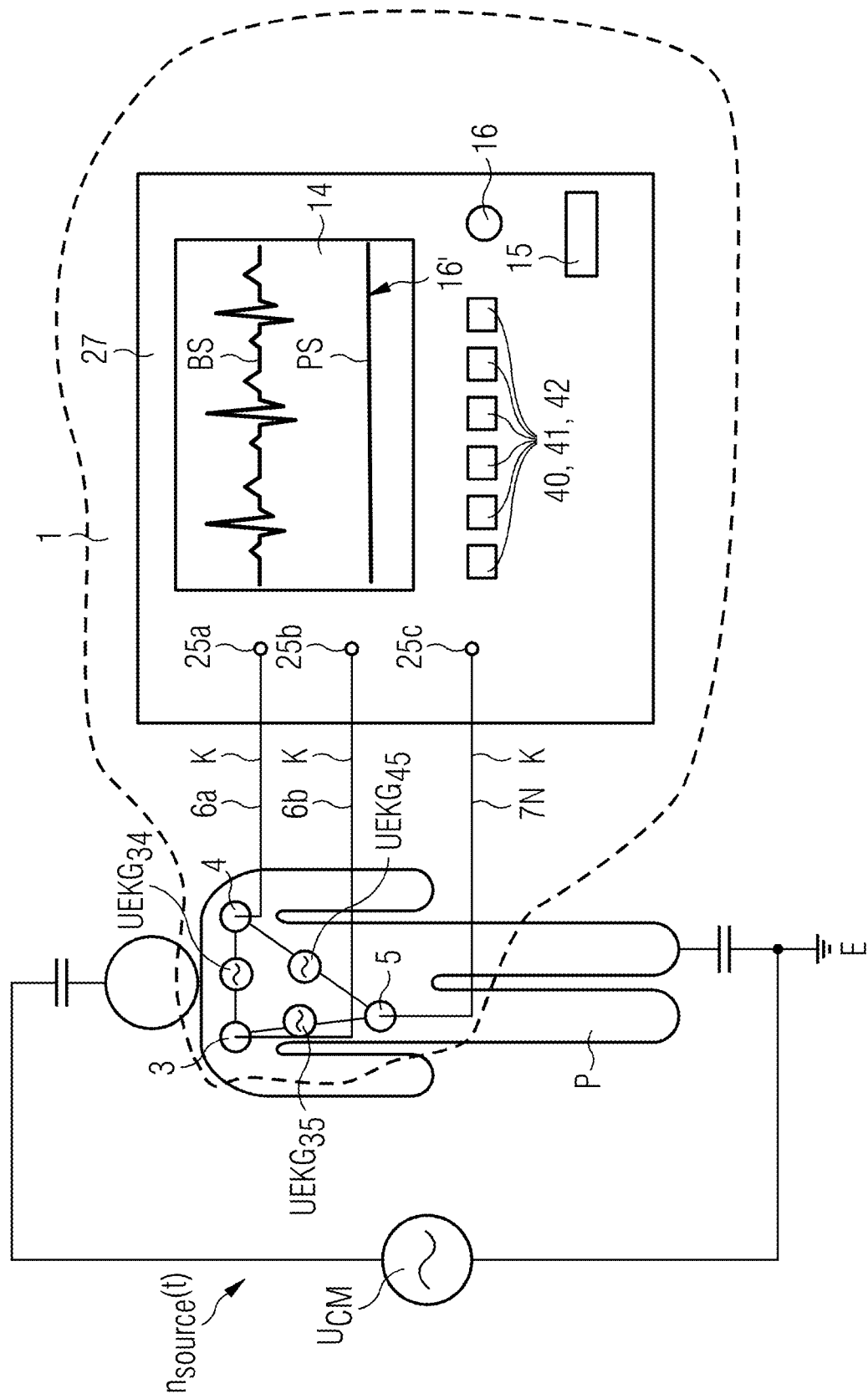
FIG. 1 schematically shows one possibility for positioning the electrical connectors or contacts of an ECG measuring system on the patient.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

In a voltage measuring system, an embodiment of the inventive fault detection device detects signal path defects, in particular cable defects in the cable, which lead, for example, from the patient to a measuring device of the differential voltage measuring system. This voltage measuring system, preferably a differential voltage measuring system, for example an ECG measuring system, an EEG measuring system or an EMG measuring system, has, as mentioned in the introduction, a signal measuring circuit with a number of useful signal paths or measuring leads for measuring the bioelectric signals. According to at least one embodiment of the invention, the fault detection device has at least one first electricity generating unit.

The electricity generating unit of an embodiment is designed such that it preferably impresses a random but defined signal on a first useful signal path of the signal measuring circuit of the voltage measuring system. The signal can preferably be a current which can be directly or indirectly impressed and measured. Therefore, the current can be impressed preferably by way of a current source onto a useful signal path. The current can, however, also particularly preferably be impressed on the useful signal path or regulated indirectly by way of a pull-up resistor and/or a pull-up-down resistor. The impressed current is preferably in the nanoampere range in order, for example, not to falsify measured bioelectric signals, and a threat to a patient is ruled out thereby.

To detect or measure the signal, at least one embodiment of the inventive fault detection device has at least one first comparison unit, which checks whether the impressed signal of the first useful signal path lies within a measuring range. Preferably, a defined measuring range or a threshold value can be selected for this purpose, above which it is assumed that the signal flows on the useful signal path.

A further component of the fault detection device is at least one first interference signal path, designed as a current measuring path, for current-detecting measurement of a first interference signal. When measuring bioelectric signals, for example ECG signals, as is known, common mode interference signals often occur, also called "Common Mode" signals (CM signals). They result, for example, from the mains frequency at 50 Hz.

Usually, in other words with intact useful signal paths or cables, the input impedances of the measuring leads of the cables of an ECG measuring system are so high that the interference signal, which is measured on the first interference signal path matches these common mode interference signals.

The fault detection device of at least one embodiment also comprises a signal path defect analysis unit, which is designed to detect a signal path defect in a useful signal path of the voltage measuring system. This signal path defect is inventively detected here, in at least one embodiment, if the impressed signal is not measured on the first interference signal path and the checked signal of the comparison unit lies within the measuring range. The signal path defect analysis unit can have a different design in this case. It can preferably comprise an Integrated Circuit, particularly preferably an ASIC. The signal path defect analysis unit can, however, also preferably comprise a microcontroller or another universal arithmetic unit.

With the method for the detection of signal path defects in the previously mentioned voltage measuring system, a first signal is accordingly inventively impressed on a first useful signal path via an electricity generating unit, in at least one embodiment.

A check or determination then follows, via at least one first comparison unit, as to whether the signal, which was impressed on the first useful signal path, lies within a measuring range. At the same time or even afterwards, a first interference signal is measured at least so as to detect current on at least one first interference signal path designed as a current measuring path. An analysis via a signal path defect analysis unit then takes place to detect a signal path defect in a useful signal path of the voltage measuring system if the impressed signal is not measured on the first interference signal path and the checked signal of the comparison unit lies within the measuring range.

If the useful signal path is connected, for example via an electrode, to a patient and the electricity generating unit impresses a signal, or a current on the first useful signal path, then this current discharges again across the patient and an appropriately configured return path, which is connected to a patient.

An appropriately configured return path for the current impressed on the useful signal path is preferably a low impedance return path at a common reference potential. Such a return path is formed, for example, by the interference path. Since, due to their high input impedances, the useful signal paths do not form a low impedance return flow path at the common reference potential (with intact cables), the impressed signal can only discharge across the interference signal path. The consequence of this is that it is not just the above-described interference signals that are on the interference signal path, but also the signal impressed on the useful signal path.

If the first useful signal path is not connected to the patient, since, for example, the electrode has detached itself from the patient, then the current circuit is not closed or the impedance to be overcome by the impressed signal is significantly greater.

Therefore, the voltage, which was produced by the electricity generating unit for example at the electrode of the first useful signal path, goes into saturation. The current can be detected for example indirectly by way of a resistor as a voltage. The impressed signal therefore lies outside a measuring range.

This checking, determining or measuring is carried out via the comparison unit. The comparison unit can therefore check whether the useful signal path is connected to a patient or not. On its own, however, it does not give any information on whether a signal path defect of a useful signal path, connected to a patient, exists.

If a signal measuring cable or cable of a useful signal path is defective, the signal measuring circuit, in addition to the interference signal path, has at least one further low impedance return path for the impressed current. The impressed signal then passes into the shield or ground and no longer discharges across the interference signal path. The signal on the interference signal path is therefore no longer increased by the signal impressed on the useful signal path in the case of a cable defect.

If the impressed signal cannot be detected on the interference signal path, the comparison unit indicates that the useful signal path, on which the signal was impressed, is connected to a patient, so that a signal path defect of the useful signal path, on which the signal was impressed, exists. This analysis is carried out via the signal path defect analysis unit.

The inventive device of at least one embodiment therefore firstly provides information on whether a useful signal path is connected to patient and whether a signal path defect of such a useful signal path exists.

In contrast to the prior art, in which only the useful signal paths or the cable itself for checking are checked, according to at least one embodiment of the invention, it is therefore also measured on an interference signal path and checked whether the signals additionally impressed on the useful signal paths have overcoupled onto the interference signal path.

The useful signal paths therefore have a dual function here. They are used firstly to measure bioelectric signals, so that they constitute part of the signal measuring circuit. Secondly, currents are impressed on the useful signal paths to detect whether they overcouple on an interference signal path, so that the useful signal paths also constitute part of the fault detection device.

One advantage of the inventive devices and methods of embodiments described here, is that a technician or service person is no longer required in order to detect a cable defect. The measurement on the interference signal path and on the useful signal path can proceed simultaneously and automatically during a useful signal measurement and a cable defect can be rendered immediately visible, for example on a user interface of the voltage measuring system. Therefore, the signal path defect, or cable defect, can be discovered immediately, for example by the operator themselves, and the cable can be replaced immediately and a correct measurement can be carried out. This consequently reduces the risk of measurements continuing to be made with undetected damaged cables.

Furthermore, the useful signal does not play any part in the detection of a signal path defect. Therefore, the inventive fault detection device of at least one embodiment can be used for a wide variety of voltage measuring systems, such as, for example ECG measuring systems, EEG measuring systems or EMG measuring systems, without having to be specifically adapted for this. Enormous development and production cost savings can likewise be made hereby.

Furthermore, the fault detection device does not require any external voltage source for detection of a signal path defect, since all relevant current-carrying parts are integrated in the fault detection device or the voltage measuring device. The test structure can be completely passive as a result.

The inventive fault detection device of at least one embodiment can be an independent component and be fitted or connected upstream or interconnected, for example as a retrofit kit in existing ECGs, EEGs or EMGs, for example by way of plug-in connectors, and this will be explained in more detail later. Preferably, the fault detection device is already permanently integrated in an inventive voltage measuring system of at least one embodiment, however.

A large proportion of the above-mentioned components of the voltage measuring device, in particular the signal path defect analysis unit, can be wholly or partially implemented in the form of software modules in a processor of a corresponding voltage measuring system. An implementation largely in terms of software has the advantage that even previously used voltage measuring systems can be easily retrofitted by way of a software update in order to operate inventively in at least one embodiment. In this regard the object is also achieved by a corresponding computer program—product having a computer program, which can be loaded directly into a storage device of a voltage measuring system, having program segments in order to carry out all steps of at least one embodiment of the inventive method when the program is run in the voltage measuring system.

In addition to the computer program, a computer program product of this kind can optionally comprise additional components, such as, for example documentation and/or additional components also hardware components, such as, for example hardware keys (dongles, etc.) in order to utilize the software.

A computer-readable medium, for example a memory stick, a hard disk or another portable or permanently fitted data carrier, on which the program segments of the computer program, which can be read-in and executed by an arithmetic unit of the voltage measuring system are stored, can be used for transportation to the voltage measuring system and/or for storage on or in the voltage measuring system. The arithmetic unit can have one or more cooperating microprocessor(s) or the like for this purpose.

Further, particularly advantageous embodiments and developments of the invention emerge from the claims and the following description, wherein the claims of one category can also be developed analogously to the claims and parts of the description relating to a different category of claims and in particular individual features of different example embodiments or variants can also be combined to form new example embodiments or variants.

With a voltage measuring system mentioned above, the signal measuring circuit can have any number of useful signal paths or signal measuring cables as a function of their application. As a rule, a signal measuring circuit, for example an ECG measuring system, has at least two useful signal paths. The useful signal paths preferably comprise electrodes, which can be applied to a patient to be examined in order to measure an electric potential applied there. The structure of the electrodes can depend on the exact type of measurement, for example whether it is an ECG measurement, an EEG measurement or an EMG measurement, and on where exactly the potential is to be measured on the patient. Suitable electrodes for different application purposes are known to a person skilled in the art.

The output of the electrodes is preferably connected to an amplification circuit, preferably by way of the signal measuring cables. The electrodes are particularly preferably connected to a differential amplifier. From the signals measured at its inputs and detected by the electrodes, this amplifier forms a differential and amplifies it. Furthermore, the signal measuring circuit has a signal detection unit, which is connected at the output of the amplification circuit in order to detect the amplified signals or for example the potentials and use them further and/or record them. For example, the signal detection unit can have an A/D converter and further components to process the digital signal further.

The signal measuring circuit of the differential voltage measuring system preferably has a third useful signal path. Furthermore, the signal measuring circuit preferably comprises a driver circuit, which is connected between a current measuring resistor and the signal detection unit. The driver circuit is also called a "Right-Leg Drive" (RLD) and is responsible for the generation of a signal, which is regulated to the mean common mode voltage of individual or all signals. The common mode interference signals already mentioned and measured above can be eliminated in the useful signal paths thereby.

The third useful signal path (or "Right-Leg Drive path") provides for a potential equalization between the patient and the differential voltage measuring system or the ECG measuring system. The electrode of the third useful signal path is preferably applied to the right leg of the patient, to which the designation "Right-Leg Drive" can be attributed. Basically, this third potential can also be detected at a different point on the patient, however.

The first interference signal path of at least one embodiment of the inventive fault detection device is also preferably connected by an electrode to the patient. Preferably, the third useful signal path can therefore coincide completely or at least partially with the first interference signal path, which will be explained in more detail below, or correspond at least in sections therewith. For example, the same electrode and the same cable can be used for the third useful signal path and the first interference signal path. It is therefore then not necessary for the operator to apply additional electrodes to the patient for at least one embodiment of the inventive signal path checking or to carry out other special measures.

The first interference signal path preferably has a current measuring unit. This current measuring unit preferably comprises a current measuring resistor, which is preferably a shunt resistor, and a voltage measuring device connected in parallel therewith.

The current measuring resistor can be connected between the third electrode and the driver circuit of the signal measuring circuit, in other words, the Right-Leg Drive.

It is preferred that the shunt resistor has at least one resistance value of 10 kΩ and at most a resistance value of 1,000 kΩ.

The voltage measuring device is preferably also a differential amplifier. The interference signal path has at the output of the voltage measuring device an interference signal detection unit to be able to process the measured interference signal further. The interference signal detection unit comprises, for example, an A/D converter and a unit for processing the digital signal further.

For example, typical features of the bioelectric signal, for example in an ECG signal the typical ECG waves, can be sought within the first interference signal or a signal resulting therefrom or further-processing signal, for example in the time and/or frequency domain.

As a rule, the interference signal on the first interference signal path has only very low direct current portions. If the signal is impressed on the useful signal path as a direct current, then this fraction can be distinguished very easily from the alternating current.

If the interference signal is already stressed, for example, by strong direct current fractions that are not constant over time, however, then it can be advantageous to impress the signal on the useful signal path as an alternating current.

The electricity generating unit or electricity generating checking unit is therefore preferably designed such that an alternating current and/or a direct current can be impressed on the useful signal paths.

The electricity generating unit is preferably designed such that the impressed signals on the useful signal paths comprise positive currents. One positive current in each case is impressed on the useful signal paths of the signal measuring circuit.

Therefore, for example a total current results, which can be overcoupled on the interference signal path, of $$I_g = I_P * N$$

$I_g$: total current
$I_P$: positive current
N: number of useful signal paths

If there is no signal path defect and all useful signal paths are connected to the patient, then, in addition to the interference signal, the total current impressed by the electricity generating units also discharges across the first interference signal path, therefore.

If the signal measuring circuit has a plurality of useful signal paths, then a saturation effect can occur if all useful signal paths are loaded with a positive current.

Therefore, the electricity generating unit is preferably designed such that it can impress different signals on the useful signal paths.

For this, the fault detection device has most particularly preferably one electricity generating unit per useful signal path. An electricity generating unit preferably comprises a current source. Particularly preferably and as already mentioned, the electricity generating unit comprises a pull-up or pull-down resistor, however, which regulates the voltages along the useful signal paths up or down and therefore indirectly affects the impressed currents on the respective useful signal path.

The electricity generating unit is preferably designed here such that it impresses a positive current on a number of useful signal paths and a negative current on a number of useful signal paths. The number of useful signal paths, on which a positive current is impressed, particularly preferably matches the number of useful signal paths on which a negative current is impressed. As a result, alternately, a useful signal path can be loaded with a positive current and a useful signal path can be loaded with a negative current. An impressed total current of:

$I_N$: negative current $$I_g = \frac{N}{2} * I_P - \frac{N}{2} * I_N$$

results.

A cable defect can then also be clearly detected by way of a missing total current fraction of a multiple of a positive current or a negative current.

The electricity generating unit particularly preferably impresses an individual signal on each useful signal path.

With a number of N useful signal paths this therefore results in a total signal $I_g$, or total current $I_g$ of:

$$I_g = I_{E1} + I_{E2} + \ldots + I_{EN}$$

If the total current on the first interference signal path cannot now be measured, but the comparison unit communicates that all electrodes are connected, then it can be quickly and easily determined on the basis of the value of the missing signal fraction which useful signal path has a signal path defect.

It is precisely with complex cable trees of up to 200 leads, as is the case, for example, with intracardial ECGs, such as, for example in angiography applications, that this enables targeted detection of the defective lead.

Instead of a complete, highly complex cable to the value of up to 1,000€, a single lead to the value of 10-20€ can be replaced therefore.

In order to check whether the impressed signals on the individual useful signal paths lie within the measuring range, the fault detection unit preferably does not comprise an overall comparison unit for all useful signal paths, and instead has a comparison unit for each useful signal path.

The comparison units preferably comprise one A/D converter each, but they particularly preferably also comprise one comparator each.

Due to possible further tolerances and parasitic currents in the voltage measuring system, the impressed signals differ per useful signal path by at least 5 nA and/or at most 20 nA. Most particularly preferably by about 10 nA.

In order to check or regulate the impressed signals, the fault detection device preferably has an electricity generating checking unit.

In order to easily discover the useful signal path, which has the defect, in the case of a signal path defect, the electricity generating unit is preferably designed such that it can individually switch the impressed signals per useful signal path. Therefore, after detection of a signal path defect, for example the impressing of a signal onto a useful signal path can be gradually deactivated in each case. If deactivation of a signal on a useful signal path does not generate a change in the total signal on the interference signal path, then this useful signal path has a cable defect.

In a particularly preferable embodiment, the fault detection device has a second interference signal path for measuring a second interference signal. This interference signal path can be established in a different way. It can be established in such a way that no bioelectric signals are coupled in. However, preferably, interference signals can be coupled in, which also occur on the first interference signal path, such as, for example the above-described common mode interference signals. The second interference signal path can preferably be used for reference measurement for the interference signal on the first interference signal path.

The second interference signal path does not have to comprise a signal measuring cable here but can correspond to a capacitive measurement or coupling to ground.

The second interference signal path preferably runs between a reference potential of the voltage measuring system or the ECG measuring system and an external reference potential, for example the ground potential. This electrical coupling preferably runs across a capacitive coupling. Since the second interference signal path is only coupled by the shared reference potential to the voltage measuring system, the second interference signal on the second interference signal path is largely independent of the input impedances of the used cable in the useful signal paths. The second interference signal path cannot be used as a return path for the signals impressed on useful signal paths, therefore. In addition, owing to the structure of the second interference signal path, the interference signal is determined largely by common mode interference signals.

For implementing the capacitive coupling the second interference signal path preferably has a conductor surface, electrically connected to the reference potential of the voltage measuring system, between the voltage measuring system and the ground potential. The conductor surface corresponds to a coupling capacitance here. The conductor surface can be implemented for example by a metal plate or foil.

The second interference signal path can have a current measuring unit. The current measuring unit can be connected preferably between the reference potential of the voltage measuring system and the capacitive connection to the external reference potential of the conductor surface. Furthermore, this current measuring unit can preferably also have a current measuring resistor and a voltage measuring device connected in parallel. The current measuring resistor is preferably a shunt resistor and the voltage measuring device is preferably a differential amplifier.

The second interference signal path can, for example at the output of the voltage measuring device, have an interference signal detection unit.

If two interference signal paths are used, preferably, the interference signal evaluation unit can be coupled between the two interference signal detection units, which detect the first and second interference signals. The interference signal evaluation unit can then preferably be set up to form a combination signal, preferably a differential signal, from the first and second interference signals. A signal path defect or cable defect can therefore be detected if the signals, which have been impressed on the useful signal paths, cannot be detected in the differential signal. The differential signal is therefore composed of the first and second interference signals.

If a current is impressed on a useful signal path as an alternating current, then it may be that this current is very similar to the current on the first interference signal path. If a differential signal is now formed from the first and second interference signals, the currents overcoupled from the useful signal path can be detected more easily.

The combination signal can also comprise, for example, a ratio of the first and second interference signals.

Preferably, the inventive fault detection device of at least one embodiment has an output unit, which is connected to the output of the interference signal evaluation unit is and/or is external, for example operates by way of a radio transmission. The output unit is used to output a detected signal path defect or to signal it immediately. This output or signaling can take place in situ, for example optically, acoustically. In addition, the signaling can be transmitted via radio, for example to a service technician. A further output form can take place as logging, for example together with the measurement data. Particularly preferably, logging is correlated time-wise with the measurement signal or the bioelectric signals to be measured. Therefore, for example with a fault that only occurs intermittently, as in the case of a loose connection, it can be documented which measured values can be used and which cannot.

In particular if the fault detection device is integrated in the voltage measuring system, the output unit is preferably included in a user interface of the voltage measuring system. As a result, for example the operator can simultaneously check the bioelectric signals on the user interface, for example a monitor, and detect a cable defect.

In the Figures an ECG measuring system 1 is in each case assumed by way of example as the differential voltage measuring system 1 in order to measure bioelectric signals BS, here ECG signals BS. Embodiments of the invention are not limited to this, however.

FIG. 1 shows, by way of example, an inventive ECG measuring system 1 of at least one embodiment, namely a schematic representation of an ECG device 27 with its electrical connectors and electrodes 3, 4, 5 connected thereto by cables K in order to measure ECG signals BS on a patient P. With the aid of the invention this ECG measuring system 1 is capable of detecting a cable defect D (as can be seen for example in FIG. 7) in one of the cables K.

To measure the ECG signals BS, at least one first electrode 3 and one second electrode 4 are required, which are attached to the patient P. The electrodes 3, 4 are connected by connectors 25a, 25b, usually plug-in connectors 25a, 25b to the ECG device 27 by signal measuring cables K. The first electrode 3 and the second electrode 4, including the signal measuring cables K, form part of a signal detection unit 9 (which will be explained in more detail later) with which the ECG signals BS can be acquired.

A third electrode 5 is used as a reference electrode to create a potential equalization between the patient P and the ECG device 27. This will be explained in more detail later. Conventionally, this third electrode 5 is attached to the right leg of the patient (for which reason it is often also called "Right-Leg Drive" or "RLD", as mentioned above). However, it can, as here too, be positioned at a different location. Furthermore, by way of further contacts, which are not shown in the Figures, on the ECG device 27, a large number of further connectors for further deductions (potential measurements) can also be attached to the patient P and used for the formation of suitable signals.

The voltage potentials UEKG34, UEKG45 and UEKG35 are formed between the individual electrodes 3, 4, 5, and these are used for measuring the ECG signals BS.

The measured ECG signals BS are shown on a user interface 14 of the ECG device 27 (see FIG. 1).

During the ECG measurement the patient P is at least capacitively coupled to the ground potential E (schematically shown in FIG. 1 by a coupling on the head and the right leg). However, they are subject to an interference source Ucm, for example an electrical field produced by the power supply with 50 Hz alternating current, and the low interference signal nsource(t) resulting therefrom present across the patient P and which constantly changes with time t, which interference signal is inevitably co-detected by the relatively sensitive measurement. Due to this interference source Ucm, as a rule interference signals across the patient P are coupled to the measuring leads in the signal measuring cables K, and this will be referred to later.

The signal measuring cables K, which lead from the first electrode 3 and the second electrode 4 to the ECG device 27, are part of the useful signal paths 6a, 6b here. The signal measuring cable K, which leads from the electrode 5 to the ECG device 27, corresponds here to part of a third useful signal path 7N. The third useful signal path 7N transfers interference signals of the interference source Ucm, which were coupled-in across the patient P and the electrodes.

To accordingly detect cable defects D, an embodiment of the inventive ECG measuring system 1 has a fault detection device 40, which will be explained in more detail later.

The cables K are checked for cable defects D with the aid of this fault detection device 40.

The test signal PS, generated by the fault detection device 40, which signals a cable defect D, can, as shown in FIG. 1, be displayed and depicted on the user interface 14 of the ECG device 27 by an output unit 16'. As a result, not just the ECG signals BS but simultaneously also the cables K can be monitored for a potential cable defect D on the user interface 14.

The output unit 16 does not have to be integrated in the user interface 14, however. The signaling can also be implemented, for example, by way of a signal lamp, for example in the form of an LED (light emitting diode) or the like, which signals a defect. However, it can additionally or alternatively also occur acoustically, for example by way of a warning tone. A further variant is also an external transfer, for example by radio, to a service technician or for output in a measuring protocol in order to thus display or log a cable defect D. In addition, the ECG device 27, as shown in FIG. 1, can have an external interface 15, in order to provide, for example, a connector for a printer, a storage device and/or even a network.

Figure 3:
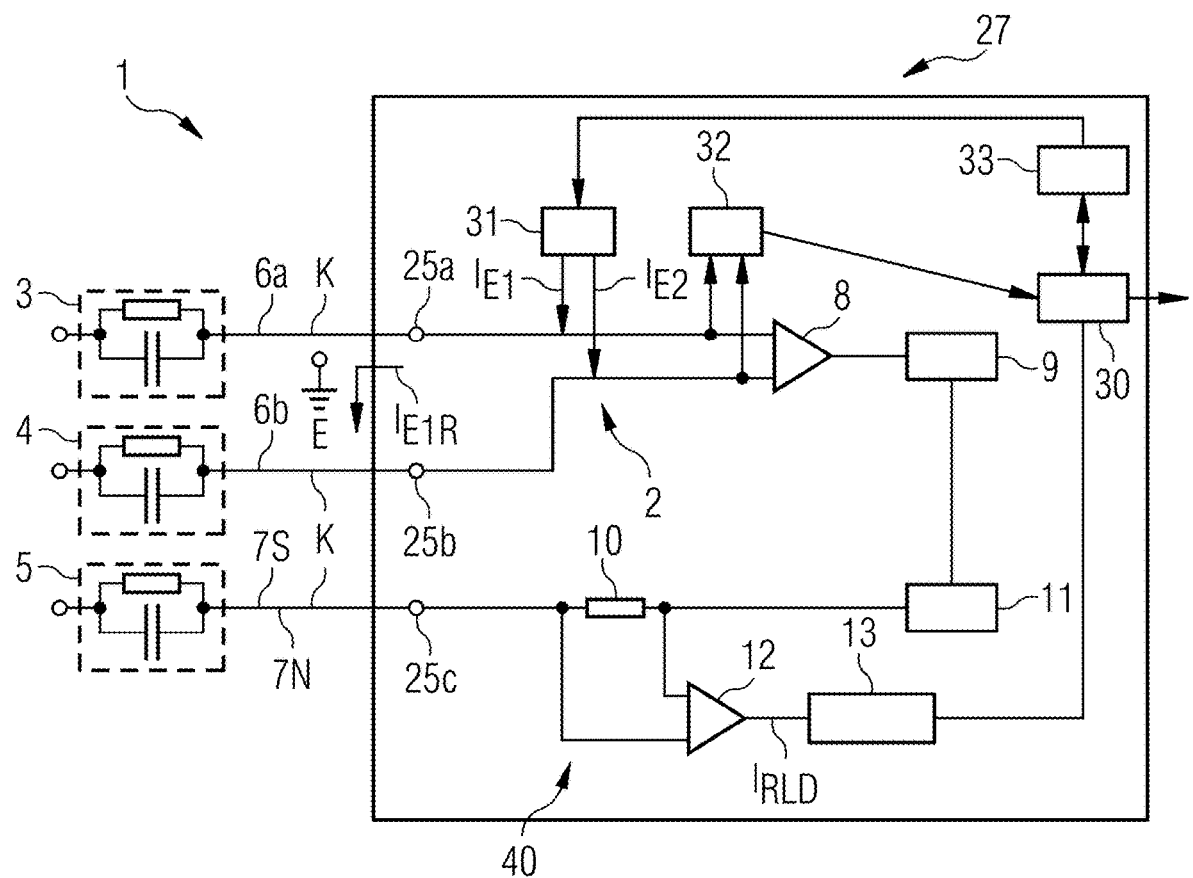

FIG. 3 illustrates extremely schematically a first example embodiment ECG device 27, for example of the ECG device 27 from FIG. 1, of an ECG measuring system 1 in a block diagram.

The ECG measuring system 1 comprises a signal measuring circuit 2, which is used for measuring the bioelectric signals BS.

The signal measuring circuit 2 has here, as already mentioned above, three useful signal paths 6a, 6b, 7N. The useful signal paths are, as described in relation to FIG. 1, electrically connected by the electrodes 3, 4, 5, the cables K and the plug-in connector 25a, 25b, 25c from the patient P to the ECG device 27. The electrodes 3, 4, 5 are shown simplified here as an RC member and illustrate the impedance values of the useful signal paths 6a, 6b, 7N.

The first electrode 3 and the second electrode 4 are in contact with the patient P. Due to a difference in potential between the discharge points, at which the electrodes 3, 4 are fastened to the patient, a useful signal, for example a "cardiac current" is transmitted from the electrodes 3, 4 to an amplification circuit 8, for example an operational amplifier. The amplification circuit 8 comprises two inputs and is electrically connected by these to the first electrode 3 and second electrode 4. The output signal of the amplification circuit 8 is transmitted to a signal detection unit 9, which detects the useful signal amplified by the amplification circuit 8. The first useful signal path 6a runs here from the contact of the first electrode 3 to the patient P via the first electrode 3 as far as the input of the amplification circuit 8. The second useful signal path 6b runs from the contact of the second electrode 4 to the patient P via the second electrode 4 to the input of the amplification circuit 8.

The third electrode 5 described in conjunction with FIG. 1 is electrically connected via the cable K to a current measuring resistor 10, hereinafter called a shunt resistor.

The shunt resistor 10 is electrically connected to a driver circuit 11 moreover, which, as already explained, is also called a Right-Leg Drive. The driver circuit 11 is constructed such that a reference potential is applied via the electrode 5 to the patient, and this matches the common mode voltages with ECG fractions. For example, this reference potential can be set in a known manner to an inverse, amplified mean of the measuring leads.

As a result, the reference potential can be fixed at the common mode voltage.

The fault detection device 40 comprises, moreover, an electricity generating unit 31. Firstly, this can impress a first signal, here a first current $I_{E1}$ in the nanoampere range, on the first useful signal path 6a. Secondly, it can impress a second signal $I_{E2}$, here a second current $I_{E2}$e in the nanoampere range, on the second useful signal path 6b. Furthermore, the second current $I_{E2}$ is here a current increased by 10 nA compared to the first current $I_{E1}$.

Currents are regulated via an electricity generating checking unit 33, which communicates with the electricity generating unit 31 and a signal path defect analysis unit 30, which will be described later.

With intact signal measuring cables, apart from the interference signal path 7S there is no further low impedance return path at the common ground potential for the first current $I_{E1}$ and the second current $I_{E2}$.

This means that there are not just interference signals $I_{CM}$ on the interference signal path 7S, but also the current $I_{E1}$ impressed on the first interference signal path 6a and the current $I_{E2}$ impressed on the second interference signal path 6b.

With intact useful signal paths 6a, 6b, the following interference signal $I_{RLD}$ therefore results on the first interference signal path 7S:

$$I_{RLD}=I_{CM}+I_{E1}+I_{E2}$$

The electricity generating unit 31 was illustrated here just once by way of example, but it can be implemented, for example, via a first current source, which impresses the first current $I_{E1}$ on the first useful signal path 6a and a second current source, which impresses the second current $I_{E2}$ on the second useful signal path 6b.

The voltages, which were generated by the electricity generating unit 31 at the first electrode 3 and the second electrode 4, are regularly at most in the millivolt range because the impressed currents discharge in the nanoampere range due to an impedance, which can be in a range from about 50 kOhm to 2 MOhm. This impedance is therefore in any case lower than that of the useful signal paths. If the first useful signal path 6a and/or the second useful signal path 6b are not electrically connected to the patient P, however, the current circuit is not closed or the impedance to be overcome by the impressed current is significantly higher.

As a result, the voltage generated by the voltage sources goes into saturation at the electrode, which has no contact with the patient P. To check this, the fault detection device 40 has a comparison unit 32. The comparison unit 32 has been illustrated here only as a block for consideration. There is a comparison unit here for the first useful signal path 6a and for the second useful signal path 6, however. The comparison units 32 here comprise comparators 32. If the determined currents on the first useful signal path 6a and on the second useful signal path 6b lies within a predefined measuring range, the first electrode 3 and the second electrode 4 are electrically connected to a patient and the comparators 32 notify two electrodes.

If, for example, only one connected electrode is notified, a user of the ECG can immediately check the electrodes and potentially re-attach them.

Figure 7:
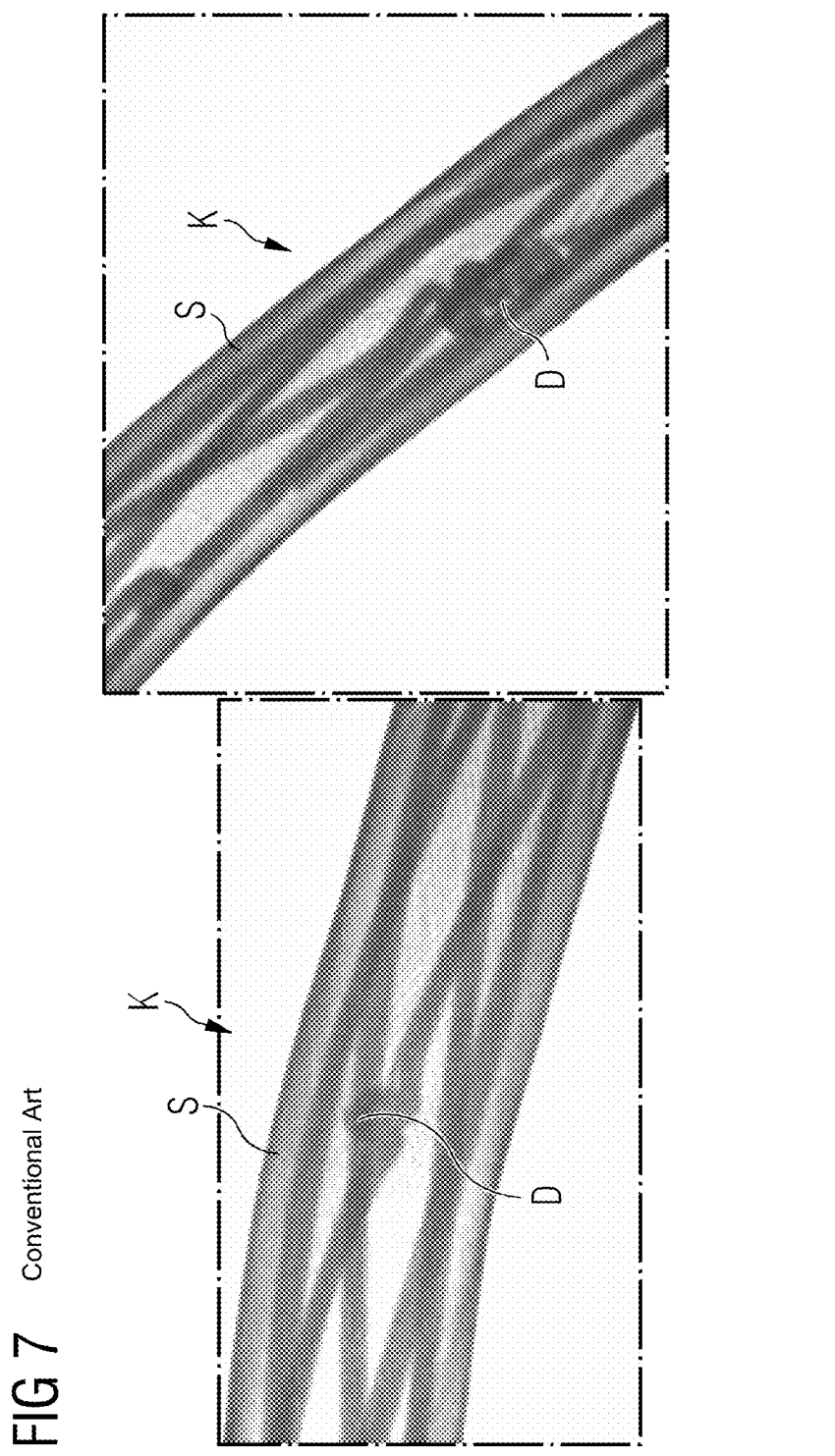
FIG. 7 shows X-ray images of two ECG cables with kinks.

As described previously, the electrodes are connected by signal measuring cables K to the ECG device 27. To make application of the ECG measuring system 1 to the patient P as simple as possible, the cables K should be narrow, light and at the same time, shielded. This combination of features often leads, however, to cable defects D, as can be seen in FIG. 7, on the x-ray images of two cables K, which are used, for example, in an ECG device 27 for measuring an ECG signal BS. The two cables K each exhibit a cable defect D in the form of a kink D here. This cable defect D can occur following bending or torsion of the cable K. Irreversible bulging of the measuring leads can occur in this connection, and this ruptures the lead insulation. Contact between the measuring leads and the shielding S can result due to the rupturing of the lead insulation. This contact results in a reduction in the input impedance and in an intensification of faults.

The reduction in the input impedance of the cable K in the case of a cable defect D, results in a further low impedance return flow path for the respective impressed current. If, for example, there is a cable defect D of the first useful signal path 6a, the current $I_{E1}$ discharges via a return path $I_{E1R}$ to ground E (and this has been drawn by way of example here) and therefore no longer increases the current IRLD on the interference signal path 7S. The comparator 32 does not detect this current which has discharged incorrectly, however, and continues to indicate that the electrode 3 is electrically connected to the patient P.

To be able to now detect this cable defect D, the inventive voltage measuring system 1 of at least one embodiment, for the above-described signal measuring circuit 2 has a first example embodiment of an inventive fault detection device 40, which comprises the interference signal path 7S.

The useful signal paths 6a, 6b comprise the first electrode 3 and the second electrode 4, the cables K, the electricity generating unit 31, the comparison unit 32 and the further lead inside the device (with the amplification circuit 8) through to the signal detection unit 9 likewise has a dual function here. Firstly, they form part of the signal measuring circuit 2 in order to measure bioelectric signals BS. Secondly, they form part of the fault detection device 40, 41, 42 in order to check whether or possibly how many electrodes of the corresponding useful signal paths 6a, 6b are connected to a patient or are defective.

The signal $I_{RLD}$ output by the interference signal evaluation unit 13 is analyzed together with the data of the comparison unit 32 in a signal path defect analysis unit 30. If the comparison units 32 communicate that all electrodes are connected and the interference signal evaluation unit 13 outputs a current $I_{RLD}$, which comprises the interference signals $I_{CM}$ and the first impressed current $I_{E1}$ and the second impressed current $I_{E2}$, the signal path defect analysis unit 30 detects that all electrodes are connected to the patient P and there is no cable defect D.

If the comparison units 32 communicate that all electrodes 3, 4 are connected but the interference signal evaluation unit 13 outputs a current $I_{RLD}$, which comprises the interference signals $I_{CM}$ and the first impressed current $I_{E1}$ but not the second impressed current $I_{E2}$, the signal path defect analysis unit 30 detects that all electrodes 3, 4 are connected to the patient P but that there is a cable defect D. Analogously, this naturally also works if both useful signal paths 6a, 6b have a signal path defect D or if only the first useful signal path 6a has a cable defect D. If, as here, the first current $I_{E1}$ and the second current IE2 differ, the signal path defect analysis unit 30 can purposefully indicate which signal path cable K has a defect D.

The fault detection device 40 does not, however, as shown for example in FIG. 3, have to be integrated in the ECG measuring system. It can also be fitted in an existing ECG measuring system by way, for example, of plug-in connectors or can also be connected upstream or interconnected. By way of such retrofitting it is possible to also detect cable defects D with an existing ECG measuring system.

To simultaneously display the ECG signals BS and possible cable defects D via a test signal PS (see FIG. 1) on the user interface 14, the latter is connected to the signal detection unit 9 of the signal measuring circuit 2 and to the signal path defect analysis unit 30 of the fault detection device 40. This is shown extremely schematically in FIG. 1. The user interface 14 is therefore shown in FIG. 1 with an output unit 16' in order to illustrate this possibility.

The above-described further output unit 16 for, for example optical and/or acoustic signaling of a cable defect D, can likewise be coupled to an output of the interference signal evaluation unit 13 and the signal path defect analysis unit 30.

Furthermore, as already mentioned, the differential voltage measuring system 1 is fitted with an external interface 15, for example for a network, a printer and/or a storage device, etc., which can be connected for signaling for example to the signal detection unit 9 of the signal measuring circuit 2 and/or signal path defect analysis unit 30.

Figure 6:
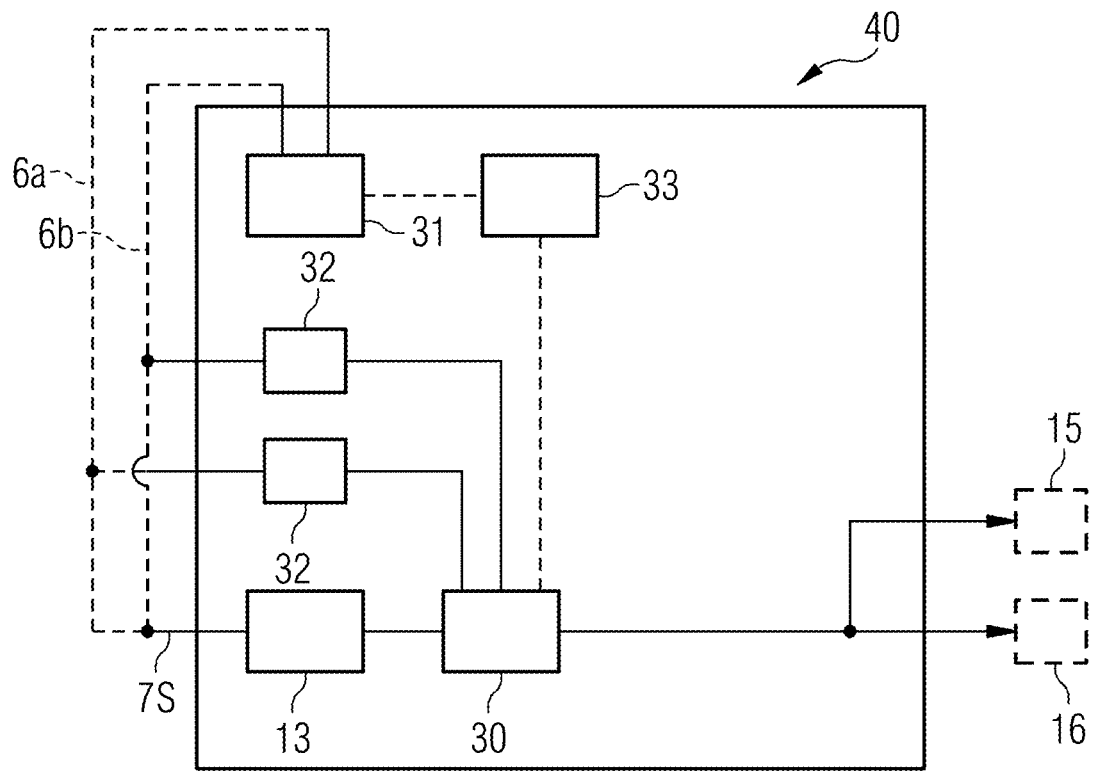

FIG. 6 shows in this regard how the signal path defect analysis unit 30 can be electrically connected to the external interface 15 and the output unit 16.

Figure 4:
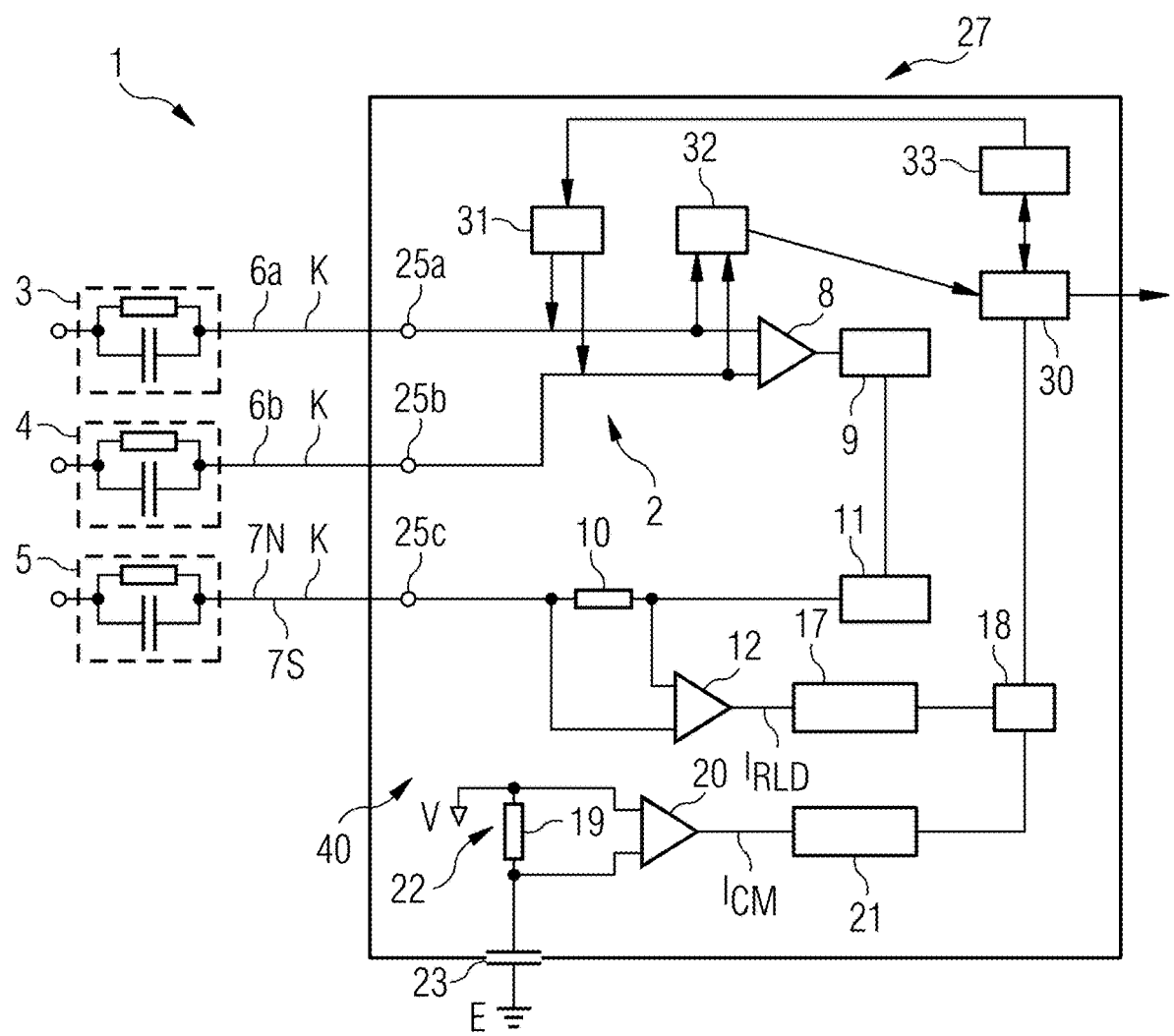

FIG. 4 shows a further inventive embodiment of the voltage measuring system 1 or the ECG measuring system 1 similar to that shown in FIG. 3. This differential voltage measuring system 1 also comprises a signal measuring circuit 2 and a fault detection device 41.

Figure 2:
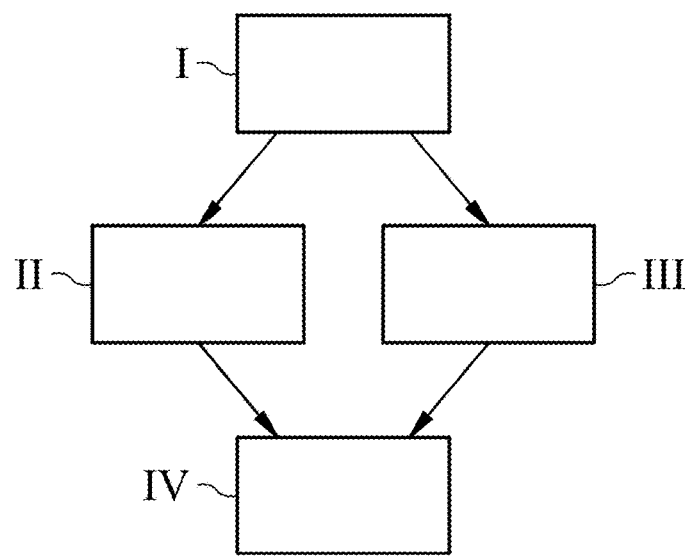
FIG. 2 shows a block diagram for one possible course of an embodiment of the inventive method, FIG. 3 schematically shows a differential voltage measuring system having a fault detection device according to a first example embodiment of the invention, FIG. 4 schematically shows a differential voltage measuring system having a fault detection device according to a second example embodiment of the invention, FIG. 5 schematically shows a differential voltage measuring system having a fault detection device according to a third example embodiment of the invention, FIG. 6 extremely schematically shows a fault detection device according to one of FIGS. 3 to 5

The signal measuring circuit 2 corresponds to the signal measuring circuit 2 described in conjunction with FIG. 2.

The fault detection device 41 represents a further example embodiment of the invention in order to detect the signal path defects D, or cable defects D. The fault detection device 41 has here two interference signal paths 7S, 22. The first interference signal path 7S comprises, as in the example embodiment in FIG. 2, the third electrode 5, which is connected by its to a patient P and runs up to the shunt resistor 10, which is electrically connected to the output of the electrode 5. Here too, the voltage that drops off across the shunt resistor 10 is measured by the first voltage measuring device 12 connected in parallel to the shunt resistor 10. The interference signal IRLD measured thereby is then digitized, processed further and detected by a first interference signal detection unit 17 connected to the output of the first voltage measuring device 12.

The fault detection device 41 also comprises a second current measuring unit 19, 20 here. The current flowing from an internal reference potential V of the ECG device 27 via a capacitive coupling to an external fixed reference potential E, the ground potential E, is measured with this second current measuring unit 19, 20. This second measured interference signal $I_{CM}$ is primarily again common mode interference signals. The capacitive coupling between the ECG device 27 and the ground potential E is always present anyway. To provide a defined interference signal path 22 for this interference signal $I_{CM}$, at which the interference signal $I_{CM}$ can be easily measured, a large-area conductor surface 23, for example in the form of a metal plate or a foil, is connected to the internal reference potential V of the ECG device 27, and this forms a "capacitor surface" to the ground potential E. The second current measuring unit 19, 20 is connected in this second interference signal path 22 between the internal reference potential V and the conductor surface 23.

For the second current measuring unit 19, 20, a current measuring resistor 19, hereinafter called a second shunt resistor, connected between internal reference potential V and conductor surface 23, and a second voltage measuring device 20 connected in parallel thereto is used for current measurement on the second interference signal path 22. The second voltage measuring device 20 can again be implemented by an amplifier, for example by a PGA.

The measured second interference signal $I_{CM}$ is detected by an interference signal detection unit 21 connected to the output of the voltage measuring device 20, for example digitized and optionally processed further by an A/D converter.

The first interference signal $I_{RLD}$, which contains common mode interference signals and with intact signal cables K of the first useful signal path 6a and the second useful signal path 6b, the overcoupled currents $I_{E1}$, $I_{E2}$, is jointly evaluated with the second interference signal $I_{CM}$, which contains only common mode interference signals, in an—here preferably digitally operating—interference signal evaluation unit 18. The interference signal evaluation unit 18 is electrically connected for this to the two interference signal detection units 17, 21.

The interference signal evaluation unit 18 is adapted here to process the first interference signal $I_{RLD}$ and the second interference signal ICM. As a result, the common mode interference on the first interference signal path 7S can be separated or distinguished from the overcoupled currents $I_{E1}$, $I_{E2}$ that occur there with intact cables K or measuring leads K. A cable defect D can be detected more easily as a consequence of this. The interference signal evaluation unit 18 can again be implemented by an arithmetic device with suitable software and/or for example also by one or more ASIC(s) for evaluation of the interference signals $I_{RLD}$, $I_{CM}$, which are indeed in digital form here.

The interference signal evaluation unit 18 can preferably be designed such that an output signal is generated from the two interference signals $I_{RLD}$, $I_{CM}$, in which the common mode interference on the first interference signal path 7S is eliminated. As a result, only the currents $I_{E1}$, $I_{E2}$ that occur with intact cables and which have been impressed on the first useful signal path 6a and the second useful signal path 6b, remain.

Figure 5:
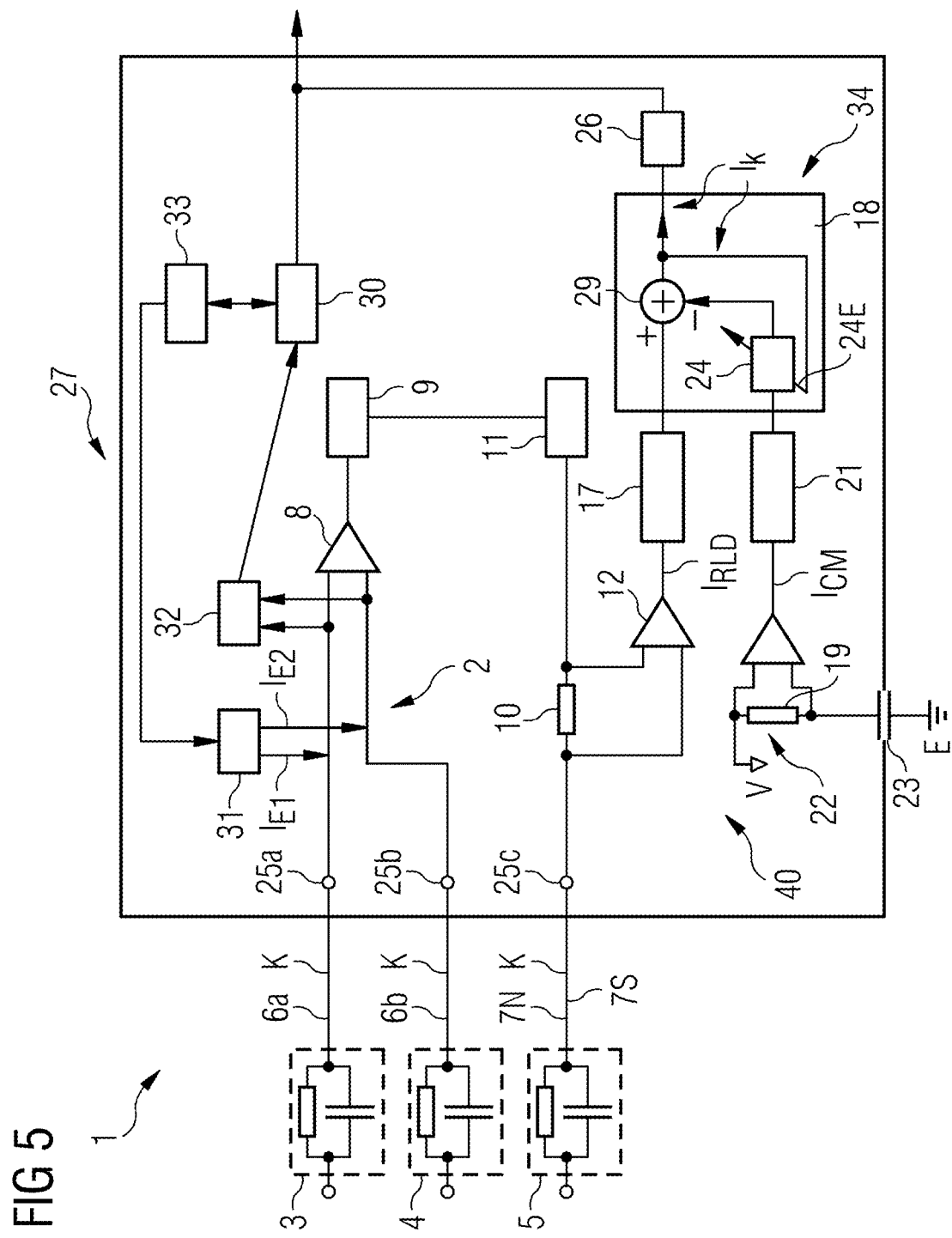

For this, some of this interference signal evaluation unit 18 can be implemented in a particularly preferable variant of the fault detection device 42, as is shown in FIG. 5, with the aid of a filter device 34. This filter device 34 filters the second interference signal $I_{CM}$ such that with a differentiation of the first and second interference signals $I_{RLD}$, $I_{CM}$ the resulting differential signal with an intact signal measuring cable K only has the currents induced by the electricity generating unit 31 (optionally with usual measurement noise).

The second interference signal $I_{CM}$ passes through a filtering process by an adaptive filter 24 in the filter device 34. A subsequent summing element 29 differentiates the first interference signal $I_{RLD}$ (which remains unchanged) and second interference signal $I_{CM}$. The adaptive filter 24 used is adjusted as a function of the two interference signals $I_{RLD}$, $I_{CM}$ or their difference here. For this purpose, a setting value input 24E, which is connected to the output of the summing element 29, is preferably subjected to the resulting differential signal $I_k$ (as a combination signal $I_k$) of the two interference signals $I_{RLD}$, $I_{CM}$.

The resulting differential signal $I_k$ can optionally be processed further, for example smoothed, by a signal processing unit 26a coupled to the output of the filter device 30 and then forms the test signal PS. Where there is no cable defect D the test signal PS then only contains the currents $I_{E1}$, $I_{E2}$ coupled in by the useful signal paths 6a, 6b. The signal processing unit 26 can then search, for example, for these currents $I_{E1}$, $I_{E2}$ to determine whether the measuring leads K are intact. This evaluation can be made for example by way of a threshold value analysis. However, a plurality of further algorithms can also be used, such as, for example pattern recognition or a Kalman filter, to evaluate the differential signal $I_k$ or combination signal $I_k$. An analysis in the time or frequency domain is also possible.

The signal measuring circuit 2 in FIG. 5 and the further structure of the fault detection device 42 match the structure from FIG. 3. For a better overview, the user interface 14, the external interface 15 and the output unit 16 are not shown, however.

The inventive fault detection devices 40, 41, 42 of at least one embodiment therefore allow a cable defect D in an ECG system 1 to be detected immediately and unambiguously. No separate test method has to be carried out by a trained service technician for this. Checking of the cables K runs simultaneously to the ECG measurement and defects D can be quickly and easily detected by any operator of the ECG device. If, moreover, different currents are impressed on the useful signal paths, it is also possible to determine which useful signal path has a signal path defect.

FIG. 2 shows a block diagram with which a method according to one example embodiment of the invention is illustrated.

In a first method step I currents are therefore impressed on the useful signal paths of a voltage measuring system.

In a subsequent method step II a check is made as to whether the currents on the useful signal paths lie in a measuring range. If the currents do not lie in the measuring range, in other words, they cannot be detected, then at least one electrode of a useful signal path is not fitted to a patient.

The method can then be stopped and a user can check the fit of the electrodes and re-attach them. Method step II can then be repeated again.

If the currents are in the measuring range, the electrodes are in contact with a patient. In method step III the current on the first interference signal path 7S is then measured. If the electrodes of the useful signal paths are connected to a patient P, as has been checked in method step 2, the impressed currents likewise flow across the interference signal path 7S and can be measured.

Method step II and method step III do not have to run consecutively. They can also take place simultaneously.

In method step IV the currents IRLD detected on the interference signal 7S are compared with the results from method step II.

If the checked currents, which have been impressed on the useful signal paths 6a, 6b, lie in the measuring range and, for example, two connected electrodes have been detected and the current measurement on the first interference signal path also measures the currents which are coupled in by two electrodes on the interference signal path, then the two electrodes are applied and there is no signal path defect.

If the checked currents, which have been impressed on the useful signal paths 6a, 6b, lie in the measuring range and, for example, two connected electrodes have been detected, but the current measurement on the first interference signal path measures for example only one current which was coupled in by an electrode on the interference signal path, then a signal path defect of a useful signal path exists.

In conclusion, it is pointed out once again that the devices and methods described in detail above are only example embodiments which can be modified by a person skilled in the art in a wide variety of ways without departing from the scope of invention. Therefore, the differential voltage measuring system can be not only an ECG device, but also other medical devices with which bioelectric signals can be detected, such as, for example EEGs, EMGs, etc. Furthermore, use of the indefinite article "a" or "an" does not preclude the relevant features from also being present several times. Similarly, the term "unit" does not preclude this from comprising a plurality of sub-components which, optionally, can be spatially distributed too.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A fault detection device for detection of signal path defects in a voltage measuring system including a signal measuring circuit for measuring bioelectric signals with a number of useful signal paths between an electrode connected to a patient and the fault detection device, the fault detection device comprising:
   at least one electricity generator, to impress a signal on a first useful signal path defined by a cable connected to an electrode at a first end of the cable, the electrode being attached to a patient, and the fault detection device at a second end of the cable and carrying a bioelectric signal;
   at least one first comparator, to determine if the signal of the first useful signal path lies within a measuring range;
   at least one first interference signal path, designed as a current measurement path, for current-detecting measurement of a first interference signal; and
   signal path defect analysis circuitry, configured to detect a signal path defect in the first useful signal path while the cable remains connected to the electrode attached to the patient and to the fault detection, and while the first useful signal path being measured is connected to the patient and receiving the bioelectric signal and upon the impressed signal not being measured on the at least one first interference signal path and upon the signal being determined, via the at least one first comparator, to lie within the measuring range, the signal path defect being a break in the cable.

2. The fault detection device of claim 1, wherein the at least one electricity generator is designed to impress different signals on the useful signal paths.

3. The fault detection device of claim 1, further comprising electricity generating checking circuitry, configured to check the signal impressed on the first useful signal path of the at least one electricity generator.

4. The fault detection device of claim 1, wherein the at least one electricity generator is designed to impress at least one of an alternating current and a direct current on the first useful signal path.

5. The fault detection device of claim 4, wherein the electricity generator is designed to switch the at least one of an alternating current and a direct current currents impressed, individually per useful signal paths.

6. The fault detection device of claim 1, wherein the electricity generator is designed such that the signal impressed on the first useful signal path includes positive currents.

7. The fault detection device of claim 1, wherein the electricity generator is designed such that a positive current is impressed on a number of the useful signal paths and a negative current is impressed on a number of the useful signal paths.

8. The fault detection device of claim 7, wherein the impressed signals differ by at least one of at least 5 nA and a maximum of 20 nA per useful signal path.

9. The fault detection device of claim 1, further comprising a second interference signal path to measure a second interference signal.

10. The fault detection device of claim 9, further comprising:
    interference signal evaluation circuitry configured to form a combination signal of the first interference signal and the second interference signal.

11. A voltage measuring system, comprising:
- at least one signal measuring circuit, including a number of useful signal paths for measuring bioelectric signals; and
- the fault detection device of claim 1.

12. The voltage measuring system of claim 11, wherein the number of useful signal paths includes at least two useful signal paths.

13. The fault detection device of claim 2, further comprising electricity generating checking circuitry, configured to check the signals respectfully impressed on the useful signal paths of the at least one electricity generator.

14. The fault detection device of claim 2, wherein the at least one electricity generator is designed to impress at least one of an alternating current and a direct current on the useful signal paths.

15. The fault detection device of claim 14, wherein the electricity generator is designed to switch the at least one of an alternating current and a direct current currents impressed, individually per useful signal paths.

16. The fault detection device of claim 2, wherein the electricity generator is designed such that the signals impressed on the useful signal paths include positive currents.

17. The fault detection device of claim 2, wherein the electricity generator is designed such that a positive current is impressed on a number of the useful signal paths and a negative current is impressed on a number of the useful signal paths.

18. The fault detection device of claim 2, wherein the impressed signals differ by at least one of at least 5 nA and a maximum of 20 nA per useful signal path.

19. The fault detection device of claim 9, further comprising:
- interference signal evaluation circuitry configured to form a differential signal of the first interference signal and the second interference signal.

20. A voltage measuring system, comprising:
- at least one signal measuring circuit, including a number of useful signal paths for measuring bioelectric signals; and
- the fault detection device of claim 2.

21. The voltage measuring system of claim 20, wherein the number of useful signal paths includes at least two useful signal paths.

22. A method for detection of signal path defects in a voltage measuring system for measuring bioelectric signals, the bioelectric signals being measured via a signal measuring circuit including a number of useful signal paths between an electrode connected to a patient and the voltage measuring system, the method comprising:
- impressing at least one first signal on at least one first useful signal path, of the number of useful signal paths, via at least one first electricity generator, the first useful signal path being defined by a cable connected to an electrode at a first end of the cable, the electrode being attached to a patient, and the voltage measuring system at a second end of the cable and carrying a bioelectric signal;
- determining, via at least one first comparator, whether the signal of the at least one first useful signal path lies within a measuring range;
- current-detecting measurement of at least one first interference signal on at least one first interference signal path designed as a current measuring path; and
- performing an analysis, via signal path defect analysis circuitry, to simultaneously detect a break in the cable representing a defect in the structural integrity of the cable in the first useful signal path of the number of useful signal paths of the voltage measuring system connected to the patient and receiving the bioelectric signal, upon the impressed signal not being measured on the at least one first interference signal path and upon the signal being determined, via the comparator, to lie within the measuring range.

23. A non-transitory computer program product storing a computer program, directly loadable into a storage device of a voltage measuring system, including program segments to carry out the method of claim 22 when the computer program is carried out in the voltage measuring system.

24. A non-transitory computer-readable medium storing a program including program segments, readable-in and executable by a processor, to carry out the method of claim 22 when the program segments are executed by the processor.

* * * * *